United States Patent
Rieger et al.

(10) Patent No.: US 6,916,893 B2
(45) Date of Patent: Jul. 12, 2005

(54) POLYMERIZATION-ACTIVE TRANSITION METAL COMPLEXES HAVING BULKY LIGAND SYSTEMS

(75) Inventors: Bernhard Rieger, Oberelchingen (DE); Markus Schmid, Ulm (DE); Robert Eberhardt, Heidenheim (DE); Michael Geprägs, Lambsheim (DE); Joachim Queisser, Mannheim (DE)

(73) Assignee: Ser. V. GmbH, Oberelchingen (DE)

(*) Notice: Subject to any disclaimer, the term of this patent is extended or adjusted under 35 U.S.C. 154(b) by 0 days.

(21) Appl. No.: 10/773,174

(22) Filed: Feb. 9, 2004

(65) Prior Publication Data

US 2004/0171774 A1 Sep. 2, 2004

Related U.S. Application Data

(63) Continuation of application No. 10/130,824, filed as application No. PCT/EP00/11813 on Nov. 27, 2000, now abandoned.

(30) Foreign Application Priority Data

Dec. 9, 1999 (DE) .......................... 199 59 251

(51) Int. Cl.$^7$ .............................. C08F 4/26; C07F 15/00
(52) U.S. Cl. .................. 526/161; 526/172; 526/165; 526/169.1; 502/103; 502/169.1; 548/108; 548/416
(58) Field of Search ................. 526/172, 161, 526/165, 169.1; 502/103, 167; 548/108, 416, 414; 546/113, 26

(56) References Cited

U.S. PATENT DOCUMENTS 5,942,461 A 8/1999 Brown et al.
6,620,896 B1 9/2003 Killian et al.

OTHER PUBLICATIONS

Brintzinger et al. Angew. Chem. Int. Ed. Engl. 34 1143–1170 (1995): "*Stereospecific Olefin Poly-merisation with Chiral Metallocene Catalysts*".
Johnson et al. J. Am. Chem. Soc. 117, 4614–4615 (1995): "*New Pd(II)– and Ni(II)–Based Cata-lysts for Polymerization of Ethylene and α–Olefins*".
Johnson et al. J. Am. Chem. Soc. 118, 267–268 (1996): "*Copolymerization of Ethylene and Pro-pylene with Functionalized Vinyl Monomers by Palladium(II) Catalysts*".
Hausmann et al. KU Kunststoffe 89(9), 154–162 (1999): "*Elastisch und schlagfest—Schlagzäh-Modifikatoren für technische Kunststoffe*".

*Primary Examiner*—Caixia Lu
(74) *Attorney, Agent, or Firm*—Novak Druce & Quigg, LLP

(57) ABSTRACT

Transition metal complexes having bulky ligand systems and the formula (I)

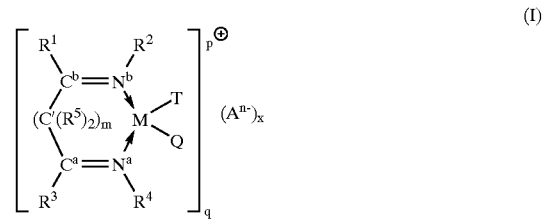

where
$R^2$, $R^4$ are $C_4$–$C_{16}$-heteroaryl or $C_6$–$C_{16}$-aryl bearing $C_4$–$C_{16}$-heteroaryl or $C_6$–$C_{16}$-aryl substituents in the two vicinal positions relative to the point of linkage to $N^a$ or $N^b$ and
M is a metal of group VIIIB of the Periodic Table of the Elements,
are described.

39 Claims, No Drawings

POLYMERIZATION-ACTIVE TRANSITION METAL COMPLEXES HAVING BULKY LIGAND SYSTEMS

This is a Continuation application of application Ser. No. 10/130,824, filed on May 23, 2002 now abandoned, the entire disclosure of which is herewith incorporated by reference, which is a National Stage Application under 35 U.S.C. §371, based on International Application No. PCT/EP 00/11813, filed Nov. 27, 2000, the entire disclosure of which is herewith incorporated by reference.

The present invention relates to polymerization-active transition metal complexes having bulky ligand systems and to a catalyst system comprising said transition metal compounds. Furthermore, the invention relates to the use of the catalyst system for preparing olefin (co)polymers and to a process for the (co)polymerization of olefinically unsaturated compounds.

Transition metal complexes as catalysts for the polymerization of olefinically unsaturated compounds are known to those skilled in the art. Catalysts based on metals of group VIB of the Periodic Table of the Elements, particularly in the form of metallocene and semisandwich complexes have become established for the coordinated polymerization of nonpolar olefins such as ethene or propene (cf. H. H. Brintzinger, D. Fischer, R. Mülhaupt, B. Rieger, R. M. Waymouth, Angew. Chem. Int. Ed. Engl. 1995, 34, 1143–1170). These complexes are generally very sensitive toward oxygen and moisture and are therefore frequently difficult to prepare and to handle. For an effective reaction, a large amount of a cocatalyst always has to be added to these metallocene complexes based on the early transition metals, which can make complicated purification steps necessary and lead to product contamination.

Brookhart et al., J. Am. Chem. Soc., 1995, 117, 6414–6415, were able to show that complexes based on the late transition metals, namely nickel and palladium complexes, can also be employed for the polymerization of ethene and propene if a bisimine compound having 2,6-diisopropylphenyl substituents on the imine nitrogen are used as chelating ligand. The 2,6-diisopropylphenyl substituents are supposed to help to shield the metal center, as a result of which chain transfer and/or elimination reactions are suppressed, which in turn makes acceptable molecular weights possible for the first time.

Furthermore, Brookhart et al., J. Am. Chem. Soc., 1996, 118, 267–268, succeeded in copolymerizing ethene with polar monomers such as methyl acrylate with the aid of the transition metal complexes described. These copolymers are, for example, used as impact modifiers for industrial plastics such as polybutylene terephthalate or polyamide because of their elastomeric properties. However, copolymers having an elastomeric property profile are mostly still prepared industrially by a free-radical route, which leads to polymers having a broad molecular weight distribution and to inhomogeneous incorporation of the olefin bearing the functional group. Such polymers are described, for example, in Hausmann et al., Kunststoffe, 1999, 9, 154.

Although copolymers having a relatively narrow molecular weight distribution can be obtained using the bisimine complexes described by Brookhart (see above), it would be desirable to have available catalyst systems which have a very high activity and at the same time are sufficiently stable under the respective polymerization conditions and have a long life, so that they are also suitable for use in industrial production. In addition, it would be desirable to provide a structurally uniform catalyst system by means of which different polymer microstructures can be obtained in a targeted manner.

It is an object of the present invention to provide transition metal complexes which are suitable as highly active polymerization catalysts for the (co)polymerization of polar or nonpolar monomers and require no or only small additions of cocatalyst components.

We have found that this object is achieved by polymerization-active transition metal complexes which have a bulky ligand system and conform to the formula (I),

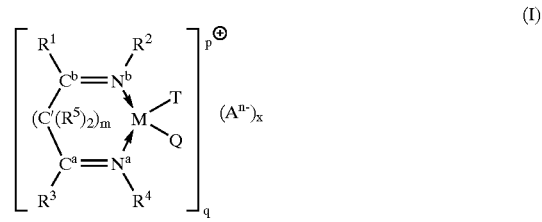

where the substituents and indices have the following meanings:

$R^1$, $R^3$ are hydrogen, $C_1$–$C_{20}$-alkyl, $C_3$–$C_{10}$-cycloalkyl, $C_6$–$C_{16}$-aryl, alkylaryl having from 1 to 10 carbon atoms in the alkyl part and from 6 to 16 carbon atoms in the aryl part, $Si(R^6)_3$, $N(R^6)(R^7)$, $OR^6$, $SR^6$ or $R^1$ and $R^3$ together with $C^a$, $C^b$ and, if present, $C'$ form a five-, six- or seven-membered aliphatic or aromatic, substituted or unsubstituted carbocyclic or heterocyclic ring, $R^2$, $R^4$ are $C_4$–$C_{16}$-heteroaryl or $C_6$–$C_{16}$-aryl bearing $C_4$–$C_{16}$-heteroaryl or $C_6$–$C_{16}$-aryl substituents in the two vicinal positions relative to the linkage point to $N^a$ or $N^b$, $R^5$ is hydrogen, $C_1$–$C_{10}$-alkyl, $C_6$–$C_{16}$-aryl or alkylaryl having from 1 to 10 carbon atoms in the alkyl part and from 6 to 16 carbon atoms in the aryl part, $R^6$, $R^7$ are $C_1$–$C_{10}$-alkyl, $C_6$–$C_{16}$-aryl or alkylaryl having from 1 to 10 carbon atoms in the alkyl part and from 6 to 16 carbon atoms in the aryl part, m is 0 or 1, M is a metal of group VIIIB of the Periodic Table of the Elements, T, Q are uncharged or monoanionic monodentate ligands or T and Q together form a diketoenolate unit or a $C_2$- or $C_3$-alkylene unit having a methyl ketone end group or a linear $C_1$–$C_4$-alkyl ester or nitrile end group A is a noncoordinating or weakly coordinating anion, x, p are 0, 1, 2 or 3 and q, n are 1, 2 or 3.

Furthermore, we have found a catalyst system comprising transition metal compounds (I) and a strong uncharged Lewis acid, an ionic compound having a Lewis-acid cation or an ionic compound having a Brönsted acid as cation as cocatalyst. We have also found the use of the transition metal compounds (I) and the catalyst system for preparing olefin (co)polymers and a process for the (co)polymerization of olefinically unsaturated compounds with the aid of the abovementioned catalyst system.

In preferred transition metal compounds (I), the substituents and indices have the following meanings:

$R^1$, $R^3$ are hydrogen, methyl, ethyl, i-propyl, t-butyl, methoxy, ethoxy, i-propoxy, t-butoxy, trifluoromethyl, phenyl, naphthyl, tolyl, 2-i-propylphenyl, 2-t-butylphenyl, 2,6-di-i-propylphenyl, 2-trifluoromethylphenyl, 4-methoxyphenyl, pyridyl or benzyl, R², R⁴ are 2,6-diphenylphenyl, 2,6-di(4'-methylphenyl) phenyl, 2,6-di(4'-t-butylphenyl)phenyl, 2,6-di(4'-methoxyphenyl)phenyl, 2,6-bis(3',5'-dimethylphenyl) phenyl or 2,6-bis(2',4',6'-trimethylphenyl)phenyl or 2,5-diphenylpyrrolidyl, 2,5-di(4'-methylphenyl)pyrrolidyl, 2,5-di(4'-t-butylphenyl)pyrrolidyl, 2,5-di(4'-methoxyphenyl)pyrrolidyl, 2,5-bis(3',5'-dimethylphenyl) pyrrolidyl or 2,5-bis(2',4',6'-trimethylphenyl)pyrrolidyl or 2,5-diphenylpyrrolide, 2,5-di(4'-methylphenyl)pyrrolide, 2,5-di(4'-t-butylphenyl)pyrrolide, 2,5-di(4'-methoxyphenyl)pyrrolide, 2,5-bis(3',5'-dimethylphenyl) pyrrolide or 2,5-bis(2',4',6'-trimethylphenyl)pyrrolide, m is 0, M is Pd or Ni, T is a halide or sulfonate ion, Q is a halide or sulfonate ion or a $C_1$–$C_6$-alkyl radical, A is a noncoordinating or weakly coordinating anion, x, p are 0 or 1 and q, n are 1 or 2.

The radicals $R^2$ and $R^4$ are $C_4$–$C_{16}$-heteroaryl or $C_6$–$C_{16}$-aryl groups which each bear $C_4$–$C_{16}$-heteroaryl or $C_6$–$C_{16}$-aryl groups in the two vicinal positions relative to the linkage point between the imine nitrogen $N^a$ or $N^b$ and the aryl or heteroaryl radical, i.e., for example in the case of a phenyl radical, in the two ortho positions relative to the covalent bond between the phenyl radical and the imine nitrogen. These positions in the radicals $R^2$ and $R^4$ can be substituted by identical or different aryl or heteroaryl groups. These heteroaryl and aryl groups can in turn themselves be substituted by functional groups based on elements of groups IVA, VA, VIA and VIIA of the Periodic Table of the Elements. Likewise, the heteroaryl or aryl radicals $R^2$ and $R^4$ can have, apart from the abovementioned substituted or unsubstituted heteroaryl or aryl radicals located in the vicinal positions, one or more further substituents based on elements of groups IVA, VA, VIA and VIIA of the Periodic Table of the Elements. Suitable functional groups are, for example, linear or branched $C_1$–$C_{10}$-alkyl, preferably $C_1$–$C_6$-alkyl, such as methyl, ethyl, n- or i-propyl, n-, i- or t-butyl, partially halogenated or perhalogenated $C_1$–$C_{10}$-alkyl, preferably $C_1$–$C_6$-alkyl, e.g. trifluoromethyl or trichloromethyl or 2,2,2-trifluoroethyl, triorganosilyl such as trimethylsilyl, triethylsilyl, tri-t-butylsilyl, triphenylsilyl or t-butyldiphenylsilyl, nitro, cyano or sulfonato, amino, for example, $NH_2$, dimethylamino, di-i-propylamino, di-n-butylamino, diphenylamino or dibenzylamino, $C_1$–$C_{10}$-alkoxy, preferably $C_1$–$C_6$-alkoxy, such as methoxy, ethoxy, i-propoxy or t-butoxy, or halogen such as fluoride, chloride, bromide or iodide.

Preferred aryl radicals $R^2$ and $R^4$ are phenyl, naphthyl and anthracenyl groups, particularly preferably phenyl and naphthyl groups and very particularly preferably the phenyl group. These groups are in turn preferably substituted in their vicinal or ortho positions by phenyl radicals or substituted phenyl radicals. Suitable substituents here are methyl, i-propyl, t-butyl, methoxy, i-propoxy and t-butoxy groups, preferably in the meta position and particularly preferably in the para position. These preferred aryl radicals $R^2$, $R^4$ may bear, apart from the vicinal or ortho substituents, one or more functional groups in the further positions of the aromatic ring system. In the case of a bis-ortho-substituted phenyl radical $R^2$, $R^4$, preference is given to an additional substitution in the para position, e.g. by a methyl, i-propyl, t-butyl, methoxy, i-propoxy, t-butoxy, chloro or bromo group.

Preferred aryl radicals $R^2$ and $R^4$ are, for example, 2,6-diphenylphenyl, 2,6-di(4'-methylphenyl)phenyl, 2,6-di(4'-t-butylphenyl)phenyl and 2,6-di(4'-methoxyphenyl)phenyl and also 2,6-bis(3',5'-dimethylphenyl)phenyl and 2,6-bis(2',4',6'-trimethylphenyl)phenyl.

Suitable $C_4$–$C_{16}$-heteroaryl radicals $R^2$ and $R^4$ can likewise bear, apart from the vicinal substituents described for aryl radicals, functional groups based on elements of groups IVA, VA, VIA or VIIA of the Periodic Table in the further positions of the heteroaryl radicals. Preference is given to $C_4$–$C_{13}$-heteroaryl radicals, particularly preferably $C_4$–$C_9$-heteroaryl radicals such as the pyrrolidyl group (linked to the imine nitrogen via a ring carbon) or the pyrrolide group (linked to the imine nitrogen via the pyrrole nitrogen) or the imidazolyl (C—N-bonded), imidazolide (N—N-bonded), benzimidazolyl, benzimidazolide, pyrazolyl, pyrazolide, pyridinyl, pyrimidinyl, quinolyl or isoquinolyl groups. Among these, the bis-ortho-substituted pyrrolidyl radical and especially the bis-ortho-substituted pyrrolide radical deserve emphasis. As ortho substituents, the phenyl group or substituted phenyl radicals are preferred. Suitable substituents here are methyl, i-propyl, t-butyl, methoxy, i-propoxy and t-butoxy groups, preferably in the meta position and particularly preferably in the para position.

Particularly preferred heteroaryl radicals $R^2$, $R^4$ are 2,5-diphenylpyrrolidyl, 2,5-di(4'-methylphenyl)pyrrolidyl, 2,5-di(4'-t-butylphenyl)pyrrolidyl and 2,5-di-(4'-methoxyphenyl)pyrrolidyl and also the corresponding 2,5-pyrrolide substituents.

Suitable radicals $R^1$ and $R^3$ in (I) are hydrogen, $C_1$–$C_{10}$-alkyl, $C_3$–$C_{10}$-cycloalkyl, $C_6$–$C_{16}$-aryl, alkylaryl having from 1 to 10 carbon atoms in the alkyl part and from 6 to 16 carbon atoms in the aryl part, a silyl radical (—Si($R^6$)$_3$), amino radical (—N($R^6$)($R^7$)), ether radical (—O$R^6$) or thioether radical (—S$R^6$). Furthermore, the radicals $R^1$ and $R^3$ together with $C^a$, $C^b$ and, if present, C' may form a five-, six- or seven-membered aliphatic or aromatic, substituted or unsubstituted carbocyclic or heterocyclic ring. Among the radicals $R^1$ and $R^3$, preference is given to hydrogen, methyl, ethyl, i-propyl, t-butyl, methoxy, ethoxy, i-propoxy, t-butoxy, trifluoromethyl, phenyl, naphthyl, tolyl, 2-i-propylphenyl, 2-t-butylphenyl, 2,6-di-i-propylphenyl, 2-trifluoromethylphenyl, 4-methoxyphenyl, pyridyl or benzyl, in particular hydrogen, methyl, ethyl, i-propyl or t-butyl. Ligand compounds containing these radicals are described in K. Vrieze and G. van Koten, Adv. Organomet. Chem., 1982, 21, 151–239. Among these cyclic systems, preferably formed by $R^1$, $R^3$, $C^a$ and $C^b$, preference is given to aromatic systems, in particular phenanthrene and camphor systems (cf. J. Matei, T. Lixandru, Bul. Inst. Politeh. Isai, 1967, 13, 245). Further preferred heterocyclic systems $R^1$, $R^3$ are 1,4-dithianes as described in WO 98/37110.

The radical $R^5$ is preferably hydrogen or methyl, in particular hydrogen.

Suitable metals M in (I) are all elements of group VIIIB of the Periodic Table of the Elements, i.e. iron, cobalt, nickel, ruthenium, rhodium, palladium, osmium, iridium or platinum. Preference is given to using nickel, rhodium, palladium or platinum, particularly preferably nickel and palladium. In the metal compounds (I), iron and cobalt are generally present in doubly or triply positively charged form, palladium, platinum and nickel are present in doubly positively charged form and rhodium is present in singly or triply positively charged form.

T and Q are, in one embodiment, uncharged and/or monoanionic monodentate ligands. Suitable uncharged ligands are Lewis bases, for example acetonitrile, benzonitrile, diethyl ether, tetrahydrofuran, amines, ketones, phosphines, ethyl acetate, dimethyl sulfoxide, dimethylformamide or hexamethylphosporamide. Ethene or an olefinically unsaturated compound in general is likewise suitable as uncharged Lewis-base ligand. Examples of monoanionic ligands are carbanions based on substituted or unsubstituted alkyl, aryl or acyl groups or halide, sulfonate or borate ions.

T in (I) is preferably a monoanionic group such as sulfonate, borate, chloride, bromide or iodide, methyl, phenyl, benzyl or a $C_1$–$C_{10}$-alkyl, which has no hydrogen atoms in the β position relative to the metal center M. This also includes groups which have a $C_1$–$C_4$-alkyl ester end group or a nitrile end group.

Particularly suitable ligands T are trifluoromethylsulfonate or halides, preferably chloride, particularly when M=Pd, or bromide, particularly when M=Ni, and also methyl as alkyl group.

Q is preferably a ligand such as acetonitrile, benzonitrile, ethene, triphenylphosphine as monodentate phosphorus compound, pyridine as monodentate aromatic nitrogen compound, acetate, propionate or butyrate, in particular acetate as suitable carboxylate, a linear alkyl ether, e.g. a linear di-$C_2$–$C_6$-alkyl ether such as diethyl ether or di-i-propyl ether, preferably diethyl ether, a cyclic alkyl ether such as tetrahydrofuran or dioxane, preferably tetrahydrofuran, a linear $C_1$–$C_4$-alkyl ester, e.g. ethyl acetate, dimethyl sulfoxide, dimethylformamide, hexamethylphosphoramide or a halide, borate or sulfonate ion. In the case of nickel complexes (I) (M=Ni), Q is preferably a halide, e.g. a chloride, bromide or iodide, in particular a bromide; in the case of palladium complexes (M=Pd), Q is preferably a halide, e.g. chloride, bromide or iodide, in particular chloride.

Furthermore, the radicals T and Q may together be a $C_2$–$C_3$-alkylene unit having a methyl ketone end group, a linear $C_1$–$C_4$-alkyl ester end group or a nitrile end group or a diketoenolate, e.g. acetylacetonate. In such a case, T and Q together are preferably a —$CH_2CH_2CH_2C(O)OCH_3$ unit and in this way form a six-membered ring together with M. While the terminal methylene unit forms a metal-carbon bond with M, the carbonyl group coordinates to M.

Among the nickel complexes (I), preference is given to nickel dihalide complexes, preferably nickel dichloride complexes or nickel dibromide complexes, or dimethylnickel complexes (p=0) and among these especially the nickel dibromide complexes. In preferred palladium complexes, T is an alkyl group, in particular methyl, or a halide, in particular chloride, and Q is a halide, in particular chloride.

For the purposes of the present invention, a noncoordinating or weakly coordinating anion A is an anion whose charge density on the anionic center is reduced due to electronegative groups and/or whose groups stearically shield the anionic center. Suitable anions A are, inter alia, antimonates, sulfates, sulfonates, borates, phosphates or perchlorates, e.g. $B[C_6H_3(CF_3)_2]_4$— (tetrakis(3,5-bis(trifluoromethyl)phenyl)borate), $B[C_6F_5]_4$— or $BF_4$— and also $SbF_6$—, $AlF_4$—, $AsF_6$—, $PF_6$— or trifluoroacetate ($CF_3SO_3$—). Preference is given to $B[C_6H_3(CF_3)_2]_4$—, $SbF_6$— and $PF_6$—. Particular preference is given to using borates, in particular $B[C_6H_3(CF_3)_2]_4$—. Suitable noncoordinating or weakly coordinating anions and their preparation are described, for example, by S. H. Strauss, Chem. Rev. 1993, 93, 927–942, and by W. Beck and k. Sünkel, Chem. Rev. 1988, 88, 1405–1421.

Preferred transition metal compounds (I) are, for example,
(bis-2,3-(2,6-diphenylphenylimino)butane)(methyl) palladium chloride,
(bis-2,3-(2,6-di(4'-methylphenyl))phenylimino)butane) (methyl)-palladium chloride,
(bis-2,3-(2,6-di-(4'-methoxyphenyl)phenylimino)butane) (methyl)-palladium chloride,
(bis-2,3-(2,6-di-(4'-trifluoromethylphenyl)phenylimino) butane-(methyl)palladium chloride,
(bis-2,3-(2,6-di-(4'-t-butylphenyl)phenylimino)butane) (methyl)-palladium chloride,
(bis-2,3-(2,6-diphenyl-4-methylphenylimino)butane) (methyl)-palladium chloride,
(bis-2,3-(2,6-di(4'-methylphenyl)-4-methylphenylimino) butane)-(methyl)palladium chloride,
(bis-2,3-(2,6-di(4'-methoxyphenyl)-4-methylphenylimino) butane-(methyl)palladium chloride,
(bis-2,3-(2,6-di(4'-trifluoromethylphenyl)-4-methylphenylimino)-butane)(methyl)palladium chloride,
(bis-2,3-(2,6-di(4'-t-butylphenyl)-4-methylphenylimino) butane)-(methyl)palladium chloride and
[(bis-2,3-(2,6-diphenylphenylimino)butane)(acetonitrile) (methyl)-palladium] tetrakis(3,5-bis(trifluoromethyl) phenyl)borate, (bis-2,3-(2,6-di(4'-methylphenyl) phenylimino)butane)(methyl)-palladium chloride,
(bis-2,3-(2,6-di(4'-methoxyphenyl)phenylimino)butane) (methyl)-palladium chloride,
[(bis-2,3-(2,6-di(4'-trifluoromethylphenyl)phenylimino) butane)-(acetonitrile)(methyl)palladium] tetrakis(3,5-bis (trifluoro-methyl)phenyl)borate,
[(bis-2,3-(2,6-di(4'-t-butylphenyl)phenylimino)butane)- (acetonitrile)(methyl)palladium] tetrakis(3,5-bis (trifluoro-methyl)phenyl)borate,
[(bis-2,3-(2,6-diphenyl-4-methylphenylimino)butane) (methyl)palladium chloride,
[(bis-2,3-(2,6-di(4'-methylphenyl)-4-methylphenylimino) butane)-(acetonitrile)(methyl)palladium] tetrakis(3,5-bis (trifluoro-methyl)phenyl)borate,
[(bis-2,3-(2,6-di(4'-methoxyphenyl)-4-methylphenylimino) butane)-(acetonitrile)(methyl)palladium] tetrakis(3,5-bis- (trifluoro-methyl)phenyl)borate,
[(bis-2,3-(2,6-di(4'-trifluoromethylphenyl)-4-methylphenylimino)-butane)(acetonitrile)(methyl) palladium] tetrakis(3,5-bis(tri-fluoromethyl)phenyl) borate and
[(bis-2,3-(2,6-di(4'-t-butylphenyl)-4-methylphenylimino) butane)-(acetonitrile)(methyl)palladium] tetrakis(3,5-bis (trifluoro-methyl)phenyl)borate and also the corresponding palladium and nickel dihalide complexes, in particular nickel dibromide complexes and palladium dichloride complexes of the diimine ligands mentioned here. Among the abovementioned compounds, particularly suitable compounds are those which have the 3,5-dimethylphenyl group, the 2,4,6-trimethylphenyl group, the 2,4,6-tris(i-propyl)phenyl group or the 2,4,6-tris(t-butyl)phenyl group as ortho substituents. In place of tetrakis(3,5-bis(tri-fluoromethyl)phenyl)borate ($B[C_6H_3(CF_3)_2]_4\ominus$) as counterion A, it is likewise possible to use hexafluoroantimonate or hexafluorophosphate ($PF_6\ominus$) in preferred transition metal compounds (I).

In the process of the present invention, the transition metal compound (I) can be used as catalyst as an individual compound or in the form of a mixture of a plurality of different transition metal compounds (I). Particularly suitable polymerization-active transition metal compounds which do not require a cocatalyst are the abovementioned methylpalladium complexes with acetonitrile as Lewis base ligand and a borate, hexafluorophosphate or hexafluoroantimonate as counteranion A.

The transition metal compounds (I) have a bidentate bisimine chelating ligand as structural element (in formula (I), that structural element which is obtained when the components M, T, Q and A are taken away). These bidentate ligands can be obtained, for example, from glyoxal or diacetyl by reaction with primary amines such as 2,6-diphenylaniline, 2,6-di(4'-methylphenyl)aniline, 2,6-di(4'-t-butylphenyl)aniline or 2,6-di-(4'-methoxyphenyl)aniline.

The latter compounds are obtainable in a simple manner from primary amines such as 2,6-dibromaniline, 2,6-dichloroaniline, 2,6-dibromo-4-methylphenylamine or 2,6-dichloro-4-methylphenylamine by means of Suzuki coupling with boronic acid derivatives in the presence of palladium catalysts (cf. Suzuki et al., Synth. Commun., 1981, 13, 513–519 and J. Am. Chem. Soc., 1989, 111, 314–321, and also Mirua et al., Synthesis, 1995, 1419–1422). The preparation of the 2,6-dihalophenyl compounds is described, for example, by C. van Koten and K. Vrieze, Adv. Organomet. Chem. 1982, Vol. 21, 152–234, Academic Press, New York.

The transition metal compounds in which p=1, 2 or 3 are obtainable, for example, from complexes in which Q is a halide, in particular a chloride, and T is methyl. In general, these complexes are treated in the presence of acetonitrile, benzonitrile, dimethylsulfoxide dimethylformamide, hexamethylphosphoramide or a linear or cyclic ether such as diethyl ether with an alkali metal or silver salt $(M^1)^+A^-$, where A is a noncoordinating or weakly coordinating anion as defined above and $M^1$ is, for example, a sodium, potassium, lithium, cesium or silver cation, i.e., for example, sodium (tetra(3,5-bis(trifluoromethyl)phenyl)borate) or silver hexafluoroantimonate. Reference may be made, for example, to the preparation of compounds of the formula (I) described by Mecking et al., J. Am. Chem. Soc., 1998, 120, 888–899.

The starting compound in which Q is a halide can be obtained by treating an appropriate cyclooctadiene complex with a bidentate bisimine chelating ligand in a noncoordinating solvent such as dichloromethane. Such preparative methods are known to those skilled in the art and are described, for example, by Johnson et al., J. Am. Chem. Soc. 1995, 117, 6414, and J. H. Groen et al., Organometallics, 1997, 17, 68. For the preparation of the cyclooctadiene complexes, reference may be made, for example, to H. Tom Dieck et al., Z. Naturforschung, 1981, 36b, 823, and D. Drew and J. R. Doyle, Inorganic Synthesis, 1990, 28, 348 and also the German Patent Application DE 19730867.

The transition metal complexes (I) can likewise be obtained starting from compounds such as $(TMEDA)MMe_2$ (TMEDA=N,N,N',N'-tetramethylethylenediamine; Me=methyl). The TMEDA complexes are obtainable, for example, from the corresponding dichloride complexes using a method described by de Graaf et al., Rec. Trav. Chim. Pay-Bas, 1988, 107, 299.

The transition metal complexes (I) can also be obtained starting from Lewis base adducts of the metal salts, e.g. bis(acetonitrile)palladium(II) chloride by treatment with a bidentate bisimine chelating ligand (cf. G. K. Anderson, M. Lin, Inorg. Synth., 1990, 28, 61, and R. R. Thomas, A. Sen, Inorg. Synth., 1990, 28, 63). The resulting metal-dimine halide complexes can be converted into the desired monoalkyl derivatives by means of alkylating reagents such as tetramethyltin $(SnMe_4)$ (cf. EP-A 0 380 162).

The starting point for the preparation of the transition metal complexes (I) is suitable metal salts or their monohydrates, dihydrates or trihydrates, e.g. cobalt (II) chloride, cobalt (II) bromide, iron(III)chloride and, in particular, nickel(II)chloride, rhodium(III)chloride, ruthenium(III) chloride, palladium(II) bromide, palladium (II) chloride or platinum(II) chloride. Particular preference is given to nickel(II)bromide or (dimethoxyethane)nickel(II) bromide $[(DME)NiBr_2]$ and palladium(II) chloride. These metal salts and their preparation are generally known from the literature and are frequently commercially available.

In a further embodiment, a cocatalyst can be used in addition to the transition metal compound (I). Suitable cocatalysts include strong uncharged Lewis acids, ionic compounds having Lewis-acid cations and ionic compounds having Brönsted acids as cations.

As strong unchanged Lewis acids, preference is given to compounds of the formula $$M^2(X^1)_a(X^2)_b(X^3)_c \qquad \text{IIa}$$

where
- $M^2$ is an alkali metal or an alkaline earth metal or an element of main group III of the Periodic Table, in particular lithium, Mg, B, Al or Ga, preferably B, and
- $X^1$, $X^2$, $X^3$ are, independently of one another, hydrogen, linear or branched $C_1$–$C_{10}$-alkyl, preferably $C_1$–$C_8$-alkyl, such as methyl, ethyl, n-propyl, i-propyl, n-butyl, i-butyl, t-butyl or n-hexyl, monosubstituted or polysubstituted $C_1$–$C_{10}$-alkyl, preferably $C_1$–$C_8$-alkyl, e.g. bearing halogen atoms such as fluorine, chlorine, bromine or iodine, $C_6$–$C_{16}$-aryl, preferably $C_6$–$C_{10}$-aryl, e.g. phenyl, which may be monosubstituted or polysubstituted, for example by halogen atoms such as fluorine, chlorine, bromine or iodine, e.g. pentafluorophenyl, alkylaryl having from 1 to 10 carbon atoms, preferably from 1 to 6 carbon atoms, in the alkyl part and from 6 to 16 carbon atoms, preferably from 6 to 10 carbon atoms, in the aryl part, e.g. benzyl, or a halide such as fluoride, chloride, bromide or iodide,
- a, b, c are each an integer from 0 to 3, where the sum a+b+c corresponds to the valence of $M^2$.

Among the radicals $X^1$, $X^2$, $X^3$, particular preference is given to those which have halogen substituents. Pentafluorophenyl may be mentioned as preferred. Particular preference is given to compounds of the formula (IIa) in which $X^1$, $X^2$ and $X^3$ are identical, preferably tris(pentafluorophenyl) borane. Further compounds (IIa) which can be used are lithium alkyls, magnesium alkyls or aluminum alkyls or aluminum halide alkyls, for example (n-butyl)(n-octyl) magnesium, triethylaluminum, tri(n-hexyl)aluminum or di-1-propylaluminum chloride.

Among the strong uncharged Lewis acids, preference is also given to using aluminoxane compounds as cocatalysts. Suitable aluminoxane compounds are essentially those compounds which have an Al—C bond. Particularly suitable cocatalysts are open-chain and/or cyclic aluminoxane compounds of the formula (IIb) or (IIc)

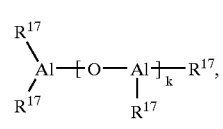

(IIb)

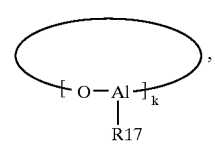

(IIc)

where
$R^{17}$ are each, independently of one another, a $C_1$–$C_4$-alkyl group, preferably a methyl or ethyl group, and k is an integer from 5 to 30, preferably from 10 to 25.

The preparation of these oligomeric aluminoxane compounds is customarily carried out by reacting a solution of trialkylaluminum with water and is described, for example, in EP-A 0 284 708 and U.S. Pat. No. 4,794,096.

The oligomeric aluminoxane compounds obtained in this way are generally in the form of mixtures of both linear and cyclic chain molecules of different lengths, so that m is to be regarded as a mean. The aluminoxane compounds can also be present in a mixture with other metal alkyls, preferably with aluminum alkyls such as triisobutylaluminum or triethylaluminum. Preference is given to using methylaluminoxane (MAO), particularly in the form of a solution in toluene. The preparation of methylaluminoxane is described in detail in, for example, EP-A 284 708.

Further cocatalysts which can be used are aryloxyaluminoxanes as described in U.S. Pat. No. 5,391,793, amidoaluminoxanes, as described in U.S. Pat. No. 5,371,260, aminoaluminoxane hydrochlorides as described in EP-A 0 633 264, siloxyaluminoxanes as described in EP-A 0 621 279 or aluminoxane mixtures.

The aluminoxanes described are used either as such or in the form of a solution or suspension, for example in aliphatic or aromatic hydrocarbons such as toluene or xylene or mixtures thereof.

Suitable ionic compounds having Lewis-acid cations have the formula $$G'^+[(L\ X^4\ X^5\ X^6\ X^7)-]_r \tag{IId}$$

where

G is an element of main group I or II of the Periodic Table of the Elements, e.g. lithium, sodium, potassium, rubidium, cesium, magnesium, calcium, strontium or barium, in particular lithium or sodium, or a silver, carbonium, oxonium, ammonium ($NH_xR'_yY$, x, y=0, 1, 2, 3 or 4, x+y=4, $R'=C_1-C_6$-alkyl or $C_6-C_{10}$-aryl), sulfonium or 1,1'-dimethylferrocenium cation, L is an element of main group III of the Periodic Table of the Elements, in particular boron, aluminum or gallium, preferably boron, $X^4$ to $X^7$ are, independently of one another, hydrogen, linear or branched $C_1-C_{10}$-alkyl, preferably $C_1-C_8$-alkyl, such as methyl, ethyl, n-propyl, i-propyl, n-butyl, i-butyl, t-butyl or n-hexyl, monosubstituted or polysubstituted $C_1-C_{10}$-alkyl, preferably $C_1-C_8$-alkyl, e.g. bearing halogen atoms such as fluorine chlorine, bromine or iodine, $C_6-C_{16}$-aryl, preferably $C_6-C_{10}$-aryl, e.g. phenyl, which may-be monosubstituted or polysubstituted, for example by halogen atoms such as fluorine, chlorine, bromine or iodine, e.g. pentafluorophenyl, alkylaryl having from 1 to 10 carbon atoms, preferably from 1 to 6 carbon atoms, in the alkyl part and from 6 to 16 carbon atoms, preferably from 6 to 10 carbon atoms, in the aryl part, e.g. benzyl, fluorine, chlorine, bromine, iodine, $C_1-C_{10}$-alkoxy, preferably $C_1-C_8$-alkoxy, such as methoxy, ethoxy or i-propoxy, or $C_6-C_{16}$-aryloxy, preferably $C_6-C_{10}$-aryloxy, e.g. phenoxy and r is 1 or 2.

The anion $(L\ X^4\ X^5\ X^6\ X^7)-$ in a compound of the formula (IId) is preferably a noncoordinating counterion. Particular mention may be made, for example, of boron compounds as are mentioned in WO 91/09882, which is hereby expressly incorporated by reference. Particularly suitable cations L are derived from the sodium or triphenylmethyl cation or from tetraalkylammonium cations, e.g. tetramethylammonium, tetraethylammonium, or tetra-n-butylammonium, or tetraalkylphosphonium cations such as tetramethylphosphonium, tetraethylphosphonium or tetra-n-butylphosphonium. Preferred compounds (IId) are, for example, sodium tetrakis(pentafluorophenyl)borate or sodium tetrakis[bis(trifluoromethyl)phenyl]borate.

Ionic compounds having Brönsted acids as cations and preferably likewise noncoordinating counterions are described in WO 91/09882, which is hereby expressly incorporated by reference. An example of a preferred cation is N,N-dimethylanilinium.

Of course, it is also possible to use mixtures of the abovementioned cocatalysts.

If T and Q in complexes (I) are each a halide, preference is given to using open-chain and/or cyclic aluminoxane compounds as cocatalyst.

On the other hand, if the complex (I) is a monoalkyl halide compound, i.e. T is, for example, an alkyl radical and Q is a halide, then an ionic compound having a Lewis-acid cation, in particular sodium tetrakis(pentafluorophenyl) borate or sodium tetrakis[bis(trifluoromethyl)phenyl]borate, is preferred as cocatalyst.

The transition metal complexes (I) or the above-described catalyst systems comprising the compound (I) make it possible to (co)polymerize polar and nonpolar olefinically unsaturated monomers.

Possible nonpolar olefinic monomers are compounds of the formula (III)

$$(R^8)HC=C(R^9)(R^{10}) \tag{III}$$

where the substituents have the following meanings:

$R^8$ to $R^{10}$ are, independently of one another, hydrogen $C_1-C_{10}$-alkyl, including both linear and branched alkyl radicals, preferably $C_1-C_6$-alkyl such as methyl, ethyl, n-, i-propyl, n-, i- or t-butyl, $C_6-C_{16}$-aryl, including aryl radicals substituted by one, two or more $C_1-C_6$-alkyl groups such as methyl, ethyl or i-propyl, e.g. tolyl, preferably $C_6-C_{10}$-aryl such as phenyl or naphthyl, in particular phenyl, alkylaryl having from 1 to 10, preferably from 1 to 6, carbon atoms in the alkyl part and from 6 to 16, preferably from 6 to 10, carbon atoms in the aryl part, e.g. benzyl, or $Si(R^{11})_3$ where $R^{11}$ is $C_1-C_{10}$-alkyl, $C_6-C_{16}$-aryl or alkylaryl having from 1 to 10 carbon atoms in the alkyl part and from 6 to 16 carbon atoms in the aryl part, where these radicals may assume the preferred or specific meanings given for $R^8$ to $R^{10}$.

Furthermore, the radicals $R^8$ and $R^9$ or $R^{10}$ together with the C=C double bond may form an unsaturated carbocycle. Suitable cyclic olefins (III) are, for example, cyclobutene, cyclopentene, cyclohexene or norbornene as well as substituted norbornenes. Among these, preference is given to cyclopentene and norbornene.

Suitable nonpolar olefinic monomers can have one, two or more terminal or internal double bonds. Preference is given to using olefinically unsaturated compounds having a terminal double bond, e.g. ethene, propene, 1-butene, 1-pentene, 1-hexene or 1-octene. Particular preference is given to ethene, propene, 1-butene and 1-hexene, in particular ethene. In addition, perfluorinated olefins such as tetrafluoroethylene are also suitable nonpolar starting monomers (III). Of course, it is also possible to use any mixtures of starting monomers (III) in the process of the present invention.

In one embodiment of the process of the present invention, α-olefins (IV) having at least one functional group in the molecule are used as further starting monomers.

Suitable functional groups are, for example, the carboxyl, carbonic ester, carboxamide, carboxylic anhydride, hydroxy, epoxy, siloxy, ether, keto, aldehyde, amino, nitrile, oxazoline, sulfonic acid, sulfonic ester or halo functionalities. Preferred functional groups are derived, inter alia, from the carboxyl unit, from carboxylic ester, carboxide or carboxylic anhydride groups or from the ether or keto group.

Preferred starting monomers (IV) are functionalized olefinically unsaturated monomers of the formula $$CH_2=C(R^{12})(R^{13}) \quad (IV)$$

where the substituents and indices have the following meanings:

$R^{12}$ is hydrogen, CN, $CF_3$, $C_1$–$C_{10}$-alkyl, $C_6$–$C_{16}$-aryl or alkylaryl having from 1 to 10 carbon atoms in the alkyl part and from 6 to 16 carbon atoms in the aryl part, pyrrolidonyl or carbazolyl, $R^{13}$ is CN, $C(O)R^{14}$, $C(O)OR^{14}$, $C(O)N(R^{14})(R^{15})$, $CH_2Si(OR^{16})_3$, $C(O)$—$O$—$C(O)R^{14}$, $O$—$C_1$— to $O$—$C_{10}$-alkyl, $O$—$C_6$- to —$O$—$C_{16}$-aryl where $R^{14}$, $R^{15}$ are hydrogen, $C_1$–$C_{10}$-alkyl, $C_2$–$C_{10}$-alkenyl, $C_6$–$C_{16}$-aryl or alkylaryl having from 1 to 10 carbon atoms in the alkyl part and from 6 to 16 carbon atoms in the aryl part, a $C_2$–$C_{10}$-alkyl group containing an epoxy group, an epoxy-substituted $C_6$–$C_{16}$-aryl group or $Si(R^{16})_3$ and $R^{16}$ is $C_1$–$C_{10}$-alkyl, $C_6$–$C_{16}$-aryl or alkylaryl having from 1 to carbon atoms in the alkyl part and from 6 to 16 carbon atoms in the aryl part.

Funktionalized olefinically unsaturated comonomers (IV) have a terminal carbon-carbon double bond. Among these compounds, (meth)acrylic acid and the ester and amide derivatives of (meth)acrylic acid, preferably acrylic acid and acrylonitrile or methacrylonitrile or mixtures thereof are particularly suitable. Preference is given to the $C_1$–$C_{10}$-alkyl, in particular the $C_1$–$C_8$-alkyl, esters of acrylic and methacrylic acid, i.e., for example, methyl, ethyl, n-, i-propyl, n-, i-, t-butyl, hexyl, dicyclopentadienyl or 2-ethylhexyl (meth)acrylate, where the alkyl radicals can be linear or branched. Also preferred are (meth)acrylates having an epoxy group in the ester unit, for example glycidyl (meth)acrylate, and also those having an alkenyl group such as ethylidene or propylidene as ester unit. Acrylates are particularly preferred. Examples of particularly suitable comonomers are methyl acrylate, ethyl acrylate, n-butyl acrylate, t-butyl acrylate, dicyclopentadienyl acrylate, glycidyl acrylate, 2-ethylhexyl acrylate and acrylic acid. Particular preference is given to methyl acrylate and glycidyl acrylate. It is likewise possible to use methacrylonitrile or acrylonitrile. Of course, any mixtures of comonomers (IV) can also be used. The abovementioned monomers are known per se and are commercially available.

The starting concentration of the functionalized monomers (IV) described can be varied over a wide range and can readily assume, for example, values in the range from 3 to 6 mol/l.

Unless expressly stated at another point, the radicals, $C_1$–$C_{10}$-alkyl, $C_3$–$C_{10}$-cycloalkyl, $C_6$–$C_{16}$-aryl and alkylaryl as substituents for the purposes of the present invention have the following general and preferred meanings. Examples of $C_1$–$C_{10}$-alkyl radicals are methyl, ethyl, n- or i-propyl, n-, i- or t-butyl and also pentyl, hexyl or heptyl groups in straight-chain and branched form. $C_1$–$C_{10}$-alkyl radicals include, except for the case of the monomer (III), those which are substituted by functional groups based on elements of groups IVA, VA, VIA and VIIA of the Periodic Table, i.e., for example, partially halogenated or perhalogenated alkyl radicals such as trichloromethyl, trifluoromethyl, 2,2,2-trifluoroethyl, pentafluoroethyl or pentachloroethyl and also alkyl radicals bearing one or more epoxy groups, for example propenoxy. For the purposes of the present invention, $C_1$–$C_{10}$-alkyl radicals are usually preferred among the $C_1$–$C_8$-alkyl radicals.

Suitable $C_3$–$C_{10}$-cycloalkyl radicals include carbocyclic and heterocyclic groups, i.e., for example, substituted and unsubstituted cyclopropyl, cyclobutyl, cyclopentyl, cyclohexyl, cyclooctyl, pyrrolidinyl, pyrrolidonyl or piperidinyl. Examples of substituted cycloaliphatic radicals are 1-methylcyclohexyl, 4-t-butylcyclohexyl and 2,3-dimethylcyclopropyl.

Suitable $C_6$–$C_{16}$-aryl groups are substituted and unsubstituted aryl radicals in general. Among the unsubstituted aryl radicals, preference is given to $C_6$–$C_{10}$-aryl groups such as phenyl and naphthyl. Phenyl is particularly preferred. In both the unsubstituted and the substituted $C_6$–$C_{16}$-aryl groups, the indicated number of carbon atoms (e.g. $C_6$-, $C_{10}$-, $C_{16}$-) refers to the number of carbon atoms forming the aromatic system. Carbon atoms from possible alkyl and/or aryl substituents are not included in this number. The expression $C_6$–$C_{16}$-aryl thus also encompasses, for example, substituted $C_6$–$C_{16}$-aryl radicals such as substituted anthracenyl. $C_6$–$C_{16}$-aryl radicals also include, except in the case of the monomer (I), radicals which are monosubstituted, polysubstituted or persubstituted by functional groups based on elements of groups IVA, VA, VIA and VIIA of the Periodic Table of the Elements. Suitable functional, groups are $C_1$–$C_{10}$-alkyl, preferably $C_1$–$C_6$-alkyl, $C_6$–$C_{16}$-aryl, preferably $C_6$–$C_{10}$-aryl, triorganosilyl such as trimethylsilyl, triethylsilyl, triphenylsilyl or t-butyldiphenylsilyl and also amino, for example, $NH_2$, dimethylamino, di-i-propylamino, di-n-butylamino, diphenylamino or dibenzylamino, $C_1$–$C_{10}$-alkoxy, preferably $C_1$–$C_6$-alkoxy, for example methoxy, ethoxy, n- or i-propoxy, n-, i- or or t-butoxy, or halogen such as fluorine, chlorine or bromine.

Suitable alkylaryl radicals include those having from 1 to 10, preferably from 1 to 6, carbon atoms in the alkyl part and from 6 to 16, preferably from 6 to 10, carbon atoms in the aryl part, in particular the benzyl group.

It has been found to be advantageous, particularly when polymerization is carried out in the presence of functionalized comonomers (IV), to add small amounts of free-radical inhibitors. Suitable free-radical inhibitors are aromatic monohydroxy compounds shielded by bulky groups, preferably phenols which have at least one bulky group in a vicinal position relative to the OH group. These free-radical inhibitors are described, for example, in DE-A 27 02 661 (=U.S. Pat. No. 4,360,617).

Suitable phenolic compounds may be found among alkylphenols, hydroxyphenylpropionates, aminophenols, bisphenols and alkylidenebisphenols. A further group of suitable phenols is derived from substituted benzocarboxylic acids, in particular from substituted benzopropionic acids.

Examples of the class of stearically hindered phenols are bis(2,6-tert-butyl)-4-methylphenol (BHT), 4-methoxymethyl-2,6-di-tert-butylphenol, 2,6-di-tert-butyl-4-hydroxymethylphenol, 1,3,5-trimethyl-2,4,6-tris(3,5-di-tert-butyl-4-hydroxybenzyl)-benzene, 4,4'-methylenebis(2,6-di-tert-butylphenol), 2,4-di-tert-butylphenyl 3,5-di-tert-butyl-4-hydroxybenzoate 2,2-bis(4-hydroxyphenyl)propane (bisphenol A), 4,4'-dihydroxybiphenyl)(DOD), 2,2'-methylenebis(4-methyl-6-tert-butylphenol), 1,6-hexanediol bis-3-(3,5-di-tert-butyl-4-hydroxyphenyl)propionate), octadecyl 3-(3,5-bis(tert-butyl)-4-hydroxyphenyl)propionate, 3,5-di-tert-butyl-4-hydroxybenzyldimethylamine,2,6,6-trioxy-1-phosphabicyclo(2.2.2)oct-4-ylmethyl 3,5-di-tert-butyl-4-hydroxyhydrocinnamate and N,N'-hexamethylenebis-3,5-di-tert-butyl-4-hydroxyhydrocinnamide. Among the above-mentioned stearically hindered phenols, preference is given to bis(2,6-($C_1$–$C_{10}$-alkyl)-4-($C_1$–$C_{10}$-alkyl)phenols, in particular bis(2,6-tert-butyl)-4-methylphenol and bis(2,6-methyl)-4-methylphenol. Particular preference is given bis(2,6-tert-butyl)-4-methylphenol.

In place of the stearically hindered phenols or in addition thereto, it is also possible to use tetraalkylpiperidin-N-oxyl radicals as free-radical inhibitors. Examples of suitable N-oxyl radicals are 2,2,6,6-tetramethyl-1-piperidinyloxy (TEMPO), 4-oxo-2,2,6,6-tetramethyl-1-piperidinyloxy(4-oxo-TEMPO), 4-hydroxy-2,2,6,6-tetramethyl-1-piperidinyloxy, 2,2,5,5-tetramethyl-1-pyrrolidinyloxy, 453-carboxy-2,2,5,5-tetramethylpyrrolidinyloxy and di-tert-butyl nitroxide. 2,6-diphenyl-2,6-dimethyl-1-piperidinyloxy and 2,5-diphenyl-2,5-dimethyl-1-pyrrolidinyloxy can likewise be used.

Of course, mixtures of various N-oxyl radicals are also possible.

The free-radical inhibitors described can be added either as such or as solutions in a suitable inert solvent, e.g. toluene or a halogenated hydrocarbon such as dichloromethane or chloroform.

In general, amounts of less than 200 ppm, less than 100 or even less than 20 ppm, based on the initial amount of functionalized olefinically unsaturated monomers, of an aromatic monohydroxy compound shielded by bulky groups or an N-oxyl radical shielded by bulky groups are sufficient to ensure that the process of the present invention proceeds in a trouble-free manner. This is likewise possible using amounts of less than 10, 5 and even 2 ppm. On the other hand, it is also possible to use concentrations of free-radical inhibitor which are twice, three times or even four times the concentration of the transition metal compound in the reaction mixture.

The preparation of the (co)polymers by the process of the present invention can be carried out in an aliphatic or aromatic aprotic solvent, e.g. in heptane, i-butane, toluene or benzene, as well as in a polar aprotic solvent. Suitable polar aprotic solvents are, for example, halogenated hydrocarbons such as dichloromethane, chloroform, carbon tetrachloride or chlorobenzene, linear or cyclic ethers such as diethyl ether or tetrahydrofuran, also acetone, dimethylsulfoxide, dimethylformamide, hexamethylphosphoramide or acetonitrile. It is of course also possible to use any, preferably homogeneous, mixtures of the abovementioned solvents. Particular preference is given to dichloromethane, chloroform, toluene, chlorobenzene and acetonitrile and also mixtures thereof, in particular toluene, chlorobenzene and dichloromethane.

The amount of solvent is usually chosen so that the starting compounds are present in dissolved form at the beginning of the reaction. The polymerization process catalyzed by the transition metal can also be carried out in bulk or in the gas phase.

In the polymerization in the gas phase, the transition metal compounds (I) can also be used in supported form. Suitable support materials are inorganic and organic materials. Suitable inorganic support materials are, for example, silica gel, aluminum oxide, magnesium oxide, titanium oxide, zirconium oxide, boron oxide, calcium oxide or zinc oxide, aluminosilicates, polysiloxanes, talc, sheet silicates, zeolites or metal halides such as $MgCl_2$. Organic support materials are derived, for example, from prepolymers of olefin (co) polymers, as are obtained, for example, using the process of the present invention. Suitable methods of application to a support are known to those skilled in the art and are described, for example, for supported Ziegler-Natta catalysts in Makromol. Chem. Phys. 1994, 195, 3347, Macromol. Rapid Commun. 1994, 15, 139–143 and Angew. Chem. Int. Ed. Engl. 1995, 34, 1143–1170, and for supported metallocene catalysts in EP-A-0 308 177 and in U.S. Pat. No. 4,897,455, U.S. Pat. No. 4,912,075 and U.S. Pat. No. 5,240,894.

The process of the present invention can be carried out either in the presence of defined transition metal compounds (I) or using the components which form the compound (I), i.e. in situ. In the latter case, it is advantageous to use a small excess of ligand, based on the metal compound.

The copolymerization is preferably carried out in the temperature range from −40 to 160° C., preferably in the range from −20 to 100° C. and particularly preferably from 0 to 80° C. The reaction times generally range from 1–2 hours to a number of days, depending on the reaction conditions chosen. In the case of gaseous reaction components such as ethene, the reaction mixture is pressurized with the respective components.

The polymerization reactions can also be carried out in the presence of hydrogen, which enables the molecular weight to be controlled. The greater the hydrogen partial pressure, the lower the molecular weight. Furthermore, the presence of hydrogen in the process described leads to a not inconsiderable increase in activity.

The compolymerization generally takes place at a pressure in the range from 0.1 to 200 bar, preferably from 0.5 to 100 bar and particularly preferably from 1 to 80 bar.

The concentration of transition metal compound (I) is generally set to a value in the range from $10^{-6}$ to 0.1 mol/l, preferably in the range from $10^{-5}$ to $10^{-2}$ mol/l and particularly preferably in the range from $5 \times 10^{-5}$ to $5 \times 10^{-2}$ mol/l.

The starting concentration of nonpolar olefin (III) is generally in the range from $10^{-3}$ to 10 mol/l, preferably in the range from $10^2$ to 5 mol/l. The starting concentration of α-olefin (IV) substituted by a functional group is generally in the range from $10^{-5}$ to 8 mol/l, preferably from $10^{-3}$ to 7 mol/l and particularly preferably from $10^{-1}$ to 6.8 mol/l.

The molar ratio of functionalized monomer to nonpolar monomer in the starting mixture is usually in the range from $10^{-3}$:1 to 1000:1, preferably in the range from $10^{-1}$:1 to 100:1, preferably from 0.1:1 to 20:1.

The initial molar ratio of free-radical inhibitors to functionalized monomer (IV) is generally in the range from $10^{-8}$:1 to $10^{-1}$:1, preferably from $10^{-7}$:1 to $10^{-2}$:1 and particularly preferably from $5 \times 10^{-7}$:1 to $10^{-4}$:1.

The polymerization can be stopped by addition of a deactivating reagent such as triphenylphosphine and/or by addition of a low molecular weight alcohol such as methanol or ethanol. If aluminum alkyl compounds or aluminoxanes are used as cocatalysts, it is advisable to use a low molecular weight alcohol.

The (co)polymers obtained by the process of the present invention have molecular weight distributions $M_w/M_n$, in the range from 1.1 to 5, preferably from 1.1 to 3.0.

The number of alkyl branches per 1000 carbon atoms in the (co)polymers obtained is usually above 15 when, for example, M=Pd in (I). In contrast, transition metal compounds (I) in which M=Ni give (co)-polymers, for example polyethylenes, having a very high degree of linearity. Accordingly, elastomeric polymers having glass transition temperatures of less than 0, preferably less than −10° C., are obtainable using palladium complexes (I). Polymers prepared using nickel complexes (I) are generally crystalline or partially crystalline and have melting points above 100° C.

The process of the present invention makes it possible to obtain homopolymers and copolymers of monomers (III) and copolymers of the monomers (III) and (IV). The process can be carried out either continuously or batchwise.

The transition metal compounds (I) have high activities, in particular also at low pressures, and additionally display no losses in activity even after a relatively long polymerization time. Furthermore, polyolefins having very high molecular weights can be obtained using the process of the present invention. In addition, the transition metal compounds (I) make it possible to prepare highly branched or linear polyolefins depending on the choice of the metal M.

The present invention is illustrated by the following examples.

EXAMPLES

Gel permeation chromatography was carried out on a Waters instrument (150C) using trichlorobenzene as eluant against a polystyrene standard. Detection was by determination of the indices of refraction.

The $^{13}$C-NMR spectra were recorded on a Bruker instrument (AC200) using $CDCl_3$ or $C_2D_2Cl_4$ as solvent. The $^1$H-NMR spectra were recorded on a Bruker instrument (AMX 500) using $CDCl_3$ or $C_2D_2Cl_4$ as solvent.

The DSC spectra were recorded on a Perkin-Elmer instrument (Series 7) at a heating rate of 20 K/min.

All work involving organometallic reagents was carried out under an inert gas atmosphere (argon). Dichloromethane was kept under reflux over calcium hydride and freshly distilled before each polymerization reaction. Benzene and toluene were kept under reflux over Na/benzophenone and likewise freshly distilled.

Phenylboronic acid was prepared by a method described by Bowie and Musgrave, J. Chem. Soc., 1966, 566–571.

Sodium tetra(3,5-bis(trifluoromethyl)phenyl)borate was prepared by the method of Brookhart et al., Organometallics, 1992, 11, 3920–3922.

A) Preparation of the Transition Metal Compound (I)
1. 2,6-diphenylphenylamine (1.a):

Phenylboronic acid (8.8 g) dissolved in ethanol (36 ml) and 2M sodium carbonate solution (72 ml) and tetrakistriphenylphosphinepalladium (3.36 g) were added to 2,6-dibromoaniline (6.02 g) in benzene (240 ml) and the reaction mixture was refluxed for 24 hours. After cooling to room temperature, the organic phase was separated off and admixed while stirring with 10.5 M hydrochloric acid (30 ml) and the product was isolated in the form of the hydrochloride salt by means of filtration. Slurrying in diethyl ether (100 ml), addition of 2 M sodium carbonate solution until the solid had dissolved while stirring and separating off the organic phase, treatment with sodium sulfate and removal of the solvent under reduced pressure gave the desired product.

$^1$H-NMR ($CDCl_3$; tetramethylsilane as standard): d 3.75 (s, $NH_2$, 2H), 6.78 (t, 1H), 7.22 (d, 2H), 7.27 (t, 2H), 7.37 (t, 4H), 7.43 (t, 4H).

In an analogous manner, 2,6-dibromoaniline was reacted with p-methoxyphenylboronic acid and with t-butylphenylboronic acid to give the corresponding phenylamines A)1.b) and A)1.c, respectively.

2. Bisimine Ligand (2.a)

p-toluenesulfonic acid (0.3 g) and diacetyl (0.48 ml) were added to 1.a) (2.45 g) in benzene (75 ml). The reaction mixture was refluxed for 72 hours using a water separator. The solvent was evaporated to a small volume under reduced pressure and the desired product was precipitated by addition of methanol.

$^1$H-NMR ($C_2D_2Cl_4$; tetramethylsilane as standard): d 1.23 (—$CH_3$, 6H), 1.38 (t-Bu, 36H), 7.1–7.5 (m, 22H).

In an analogous manner, diacetyl was reacted with the compounds A)1.b) and A)1.c) to give the corresponding diimines A)$_2$.b) and A)$_2$.c).

3. Preparation of Transition Metal Compounds (I)
3.1. Palladium Dichloro Complex (3.b)

$(PhCN)_2PdCl_2$ (1.15 g) and compound A)$_2$.b) (3.05 g) were dissolved in dichloromethane (250 ml) and stirred at RT for 72 hours. The desired metal complex was precipitated by evaporation of the solvent under reduced pressure, digested with dicloromethane (20 ml) and subsequently admixed with pentane (50 ml). The metal complex was separated off by means of filtration and washed with pentane (50 ml).

In an analogous manner, $(PhCN)_2PdCl_2$ was reacted with compounds A)$_2$.a) and A)$_2$.c) to give the corresponding palladium dichloro complexes A)3.1 a) and A)3.1 c).

3.2. Preparation of the Palladium Monomethyl Complex (4.b)

The metal complex 3.b) (0.6 g) was suspended in dichloromethane (120 ml) and admixed with tetramethyltin (0.25 ml). After stirring for 40 hours at RT, the palladium formed was separated off, the resulting solution was evaporated to a volume of 20 ml under reduced pressure and admixed with diethyl ether (about 100 ml) until the desired metal complex started to precipitate. After stirring for 30 minutes while cooling in an ice bath, the resulting solid was isolated by means of filtration, washed with diethyl ether (60 ml) and freed of the last residues of solvent under reduced pressure.

B) Polymerization Experiments in an Autoclave
1. Polymerization of Ethene Using Palladium Monomethyl Complexes Under an argon atmosphere, metal complex A)$_4$.b) (0.05 mmol), sodium tetrakis[bis(trifluoromethyl)phenyl] borate (55 mg) and dichloromethane (25 ml) were introduced. Ethene was injected, the reaction temperature was set and the ethene pressure was maintained at a constant value during the entire reaction time. After venting the reaction vessel, the polymer formed was precipitated in methanol (400 ml), filtered and freed of the last traces of solvent at 80° C. under reduced pressure.

Details regarding the amounts used, the reaction conditions and the product parameters are given in Table 1.

2. Polymerization of Ethene Using Palladium Dichloro Complexes

Under an argon atmosphere, metal complex A)3.a) (0.05 mmol), a 1.5 M solution of methylaluminoxane in toluene and toluene (25 ml) were introduced. Ethene was injected at room temperature and the reaction pressure was maintained at a constant value during the reaction time of 1 hour. After venting the reaction vessel, the polymer formed was precipitated in methanol (400 ml), filtered and freed of the last traces of solvent at 80° C. under reduced pressure.

Details regarding the amounts used, the reaction conditions and the product parameters are given in Table 2.

3. Polymerization of Ethene Using Nickel Complexes a) (DME)NiBr$_2$ (0.05 mmol) and a ligand compound A)$_2$. (see Table 3) (0.075 mmol) were suspended in toluene (25 ml) and stirred at RT for 2 hours. After addition of a 1.5 M solution of methylaluminoxane in toluene (500 equivalents), ethene was injected and the ethene pressure set was maintained at a constant value during the reaction time of 2 hours.

Details regarding the amounts used, the reaction conditions and the product parameters are shown in Table 3A.

b) (DME)NiBr$_2$ (see Table 3 B) and a ligand compound A)$_2$. (see Table 3 B; 1.1 eq)) was suspended in toluene, stirred at RT for 12 hours and activated by means of a 1.5 M solution of methylaluminoxane in toluene (500 equivalents). This catalyst mixture was introduced into a 2000 ml steel autoclave in which toluene (800 ml) was present under an argon atmosphere and which had previously been pressurized with ethene to the desired pressure (see Table 3 B).

Further details regarding the amounts used, the reaction conditions and the product parameters are shown in Table 3 B.

TABLE 1

| Experiment | Cocat./cat. [$mol_{Na}/mol_{Pd}$] | Reaction pressure [bar] | Activity [$kg/(mol_{Pd} \cdot h)$] | $T_m$ [°C.] | $T_g$ [°C.] | $M_w$ [g/mol] | $M_w/M_n$ | N[e] |
|---|---|---|---|---|---|---|---|---|
| 1 | 2 | 5 | 3.0 | 80.4 | −13.8 | 12,300 | 2.0 | n.d. |
| 2 | 2 | 20 | 9.6 | 76.2 | −13.4 | 16,100 | 2.2 | 38 |
| 3 | 2 | 30 | 14.0 | 78.1 | −16.1 | 11,600 | 1.8 | 47 |
| 4[a)b)] | 1.2 | 20 | n.d.[d] | n.d. | n.d. | 13,200 | 2.4 | n.d. |
| 5[b)] | 1.2 | 2 | 2 | 58 | n.d. | 13,300 | 1.7 | n.d. |
| 6[b)] | 1.2 | 10 | 12 | 61 | n.d. | 17,700 | 2.3 | 56 |
| 7[b)] | 1.2 | 20 | 16 | 66 | n.d. | n.d. | n.d. | 55 |
| 8[b)] | 1.2 | 30 | 20 | 66 | n.d. | 11,400 | 1.6 | 58 |
| 9[b)] | 1.2 | 40 | 16 | 65 | n.d. | n.d. | n.d. | 50 |
| 10[b)] | 1.2 | 55 | 6 | 59 | n.d. | 12,500 | 1.8 | n.d. |
| 11[c)] | 1.2 | 6 | 51.4 | −41 | −71 | 358,900 | 2.1 | 106 |

[a)]Reaction time: 20 h;
[b)]The catalyst used was compound A) 4.a);
[c)]Comparative experiment: the catalyst used was bis-2, 3-(2,6-di-i-propylphenylimino)butane) (methyl) palladium chloride, prepared by a method analogous to that described by Brookhart et al., J. Am. Chem. Soc., 1995, 117, 6414–6415; Reaction time: 20 h; reaction temperature: 35° C.;
[d)]n.d. = not determined;
[e)]Number of alkyl branches/1000 carbon atoms in the polymer backbone.

TABLE 2

| Experiment | Cocat./cat. [$mol_{Al}/mol_{Pd}$] | Reaction pressure [bar] | Activity [$kg/(mol_{Pd} \cdot h)$] | $T_m$ [°C.] | $M_w$ [g/mol] | $M_w/M_n$ | N[d] |
|---|---|---|---|---|---|---|---|
| 1 | 100 | 5 | 18.2 | 105.6 | 150,000 | 2.0 | 24 |
| 2 | 500 | 5 | 28.0 | 48.3 | 148,000 | 2.0 | n.d. |
| 3 | 100 | 30 | 19.0 | 105.3 | '95,000 | 1.7 | 27 |
| 4 | 1000 | 30 | 39.0 | n.d. | 231,000 | 1.8 | 78 |
| 5[a)] | 2000 | 30 | 60.0 | 44.8 | 275,000 | 1.5 | 69 |
| 6 | 100 | 55 | 26.0 | 105.3 | 139,000 | 2.8 | 35 |
| 7 | 500 | 55 | 50.0 | 47.9 | 274,000 | 2.5 | 61 |
| 8[b)] | 500 | 30 | 14.0 | —[c] | 407,000 | 2.1 | 99 |
| 9[b)] | 500 | 55 | 15.2 | —[c] | 437,000 | 2.0 | 111 |

[a)]The amount of catalyst used was 0.01 mmol;
[b)]Comparative experiment: the catalyst used was (bis-2, 3-(2,6-di-i-propylphenylimino)butane) palladium dichloride, prepared by a method analogous to that described by Brookhart et al., J. Am. Chem. Soc., 1995, 117, 6414–6415;
[c)]Amorphous polymer was obtained;
[d)]Number of alkyl branches/1000 carbon atoms in the polymer backbone.

TABLE 3A

| Experiment | Amount of cat. Ligand type [mmol] | Cocat./cat. [$mol_{Al}/mol_{Ni}$] | Reaction pressure [bar] | Activity [$kg/(mol_{Ni} \cdot h)$] | $T_m$ [°C.] | $M_w$ [g/mol] | $M_w/M_n$ | N[c] |
|---|---|---|---|---|---|---|---|---|
| 1[a)] | 0.01 A)2.b) | 500 | 10 | 780 | 134.7 | 3,590,000 | 3.5 | — |
| 2[a)] | 0.05 A)2.b) | 500 | 20 | 880 | 134.7 | 4,040,000 | 2.8 | — |
| 3 | 0.02 A) 2.a) | 1000 | 6 | 433 | 141.2 | n.d. | n.d. | — |
| 4[a)] | 0.01 A)2.c) | 500 | 10 | 2118 | n.d. | 3,400,000 | 3.5 | — |
| 5 | 0.02[b)] | 1000 | 6 | 309 | 42.1/66.4 | n.d. | n.d. | 77 |

[a)]Effective reaction time: 2 min;
[b)]Comparative experiment: the catalyst used was (bis-2,3-(2,6-di-i-propylphenylimino)butane)nickel dibromide, prepared by a method analogous to that described by Brookhart et al., J. Am. Chem. Soc., 1995, 117, 6414–6415;
[c)]Number of alkyl branches/1000 carbon atoms in the polymer backbone.

TABLE 3 B

| Experiment[a] | Amount of cat. Ligand type [mmol] | Cocat./Cat. [mol$_{Al}$/mol$_{Ni}$] | Reaction pressure [bar] | Activity [kg/(mol$_{Ni}$·h)] | T$_m$ [°C.] | M$_w$ (x/0$^6$)[g/mol] |
|---|---|---|---|---|---|---|
| 1 | 0.04 A)2.a) | 500 | 30 | 6000 | 132 | n.d. |
| 2 | 0.02 A)2.c) | 500 | 10 | 6,500 | 130 | >4.0 |
| 3 | 0.02 A) 2.c) | 500 | 30 | 20,000 | 130 | n.d. |

[a]Effective reaction time: 15 min;

We claim:

1. A transition metal compound of the formula

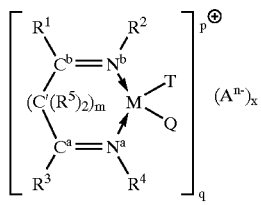

(I)

wherein:

$R^1$, $R^3$ are hydrogen, $C_1$–$C_{20}$-alkyl, $C_3$–$C_{10}$-cycloalkyl, $C_6$–$C_{16}$-aryl, alkylaryl having from 1 to 10 carbon atoms in the alkyl part and from 6 to 16 carbon atoms in the aryl part, $Si(R^6)_3$, $N(R^6)(R^7)$, $OR^6$ $SR^6$ or $R^1$ and $R^3$ together with $C^a$, $C^b$ and, if present, $C'$ form a five-, six- or seven-membered aliphatic or aromatic, substituted or unsubstituted carbocyclic or heterocyclic ring, $R^2$, $R^4$ are $C_4$–$C_{16}$-heteroaryl or $C_6$–$C_{16}$-aryl bearing $C_4$–$C_{16}$-heteroaryl or $C_6$–$C_{16}$-aryl substituents in the two vicinal positions relative to the linkage point to $N^a$ or $N^b$, $R^5$ is hydrogen, $C_1$–$C_{10}$-alkyl, $C_6$–$C_{16}$-aryl or alkylaryl having from 1 to 10 carbon atoms in the alkyl part and from 6 to 16 carbon atoms in the aryl part, $R^6$, $R^7$ are $C_1$–$C_{10}$-alkyl, $C_6$–$C_{16}$-aryl or alkylaryl having from 1 to 10 carbon atoms in the alkyl part and from 6 to 16 carbon atoms in the aryl part, m is 0 or 1, M is a metal of group VIIIB of the Periodic Table of the Elements, T, Q are uncharged or monoanionic monodentate ligands or T and Q together form a diketoenolate unit or a $C_2$— or $C_3$-alkylene unit having a methyl ketone end group or a linear $C_1$–$C_4$-alkylester or nitrile end group, A is a noncoordinating or weakly coordinating anion, x, p are 0, 1, 2 or 3 and q, n are 1, 2 or 3.

2. A transition metal compound as claimed in claim 1, wherein $R^2$ and $R^4$ are, independently of one another, 2,6-diphenylphenyl, 2,6-di(4'-methylphenyl)phenyl, 2,6-di(4'-t-butylphenyl)phenyl, 2,6-di(4'-methoxyphenyl)phenyl, 2,6-bis(3',5'-dimethylphenyl)phenyl 2,6-bis(2',4',6'-trimethylphenyl)phenyl 2,5-diphenylpyrrolidyl, 2,5-di(4'-methylphenyl)-pyrrolidyl, 2,5-di(4'-t-butylphenyl) pyrrolidyl, 2,5-di(4'-methoxyphenyl)pyrrolidyl, 2,5-bis(3', 5'-dimethylphenyl)-pyrrolidyl, 2,5-bis(2',4',6'-trimethylphenyl)pyrrolidyl, 2,5-diphenylpyrrolide, 2,5-di- (4'-methylphenyl)pyrrolide, 2,5-di(4'-t-butylphenyl) pyrrolide, 2,5-di(4'-methoxyphenyl)-pyrrolide, 2,5-bis(3',5'-dimethylphenyl)pyrrolide or 2,5-bis(2',4',6'-trimethylphenyl)pyrrolide.

3. A transition metal compound of claim 1, wherein $R^2$ and $R^4$ are 2,6-di(4'-methoxyphenyl)phenyl or 2,5-di(4'-methoxyphenyl)-pyrrolidyl.

4. The transition metal compound of claim 1, wherein M is palladium or nickel.

5. The transition metal compound of claim 1, wherein T is halide or methyl and Q is halide.

6. The transition metal compound of claim 1, wherein $R^2$ and $R^4$ are both 2,6-diphenylphenyl and m is 0.

7. The transition metal compound of claim 6, wherein $R^1$ and $R^3$ are hydrogen or methyl.

8. The transition metal compound of claim 1, wherein $R^2$ and $R^4$ are both [2,6-bis(4-t-butylphenyl)phenyl] and m is 0.

9. The transition metal compound of claim 8, wherein $R^1$ and $R^3$ are hydrogen or methyl.

10. The transition metal compound of claim 1, wherein M is Ni.

11. The transition metal compound of claim 10, wherein T and Q are chloride, bromide or iodide anions.

12. A compound of the formula

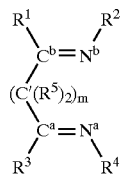

(V)

wherein:

$R^1$, $R^3$ are hydrogen, $C_1$–$C_{20}$-alkyl, $C_3$–$C_{10}$-cycloalkyl, $C_6$–$C_{16}$-aryl, alkylaryl having from 1 to 10 carbon atoms in the alkyl part and from 6 to 16 carbon atoms in the aryl part, $Si(R^6)_3$, $N(R^6)(R^7)$, $OR^6$, $SR^6$, or $R^1$ and $R^3$ together with $C^a$, $C^b$ and, if present, $C'$ form a five-, six- or seven-membered aliphatic or aromatic, substituted or unsubstituted carbocyclic or heterocyclic ring, $R^2$, $R^4$ are $C_4$–$C_{16}$-heteroaryl or $C_6$–$C_{16}$-aryl bearing $C_4$–$C_{16}$-heteroaryl or $C_6$–$C_{16}$-aryl substituents in the two vicinal positions relative to the linkage point to $N^a$ or $N^b$, $R^5$ is hydrogen, $C_1$–$C_{10}$-alkyl, $C_6$–$C_{16}$-aryl or alkylaryl having from 1 to 10 carbon atoms in the alkyl part and from 6 to 16 carbon atoms in the aryl part, $R^6$, $R^7$ are $C_1$–$C_{10}$-alkyl, $C_6$–$C_{16}$-aryl or alkylaryl having from 1 to 10 carbon atoms in the alkyl part and from 6 to 16 carbon atoms in the aryl part; and m is 0 or 1

M is a metal of group VIIIB of the Periodic Table of the Elements,

T, Q are uncharged or monoanionic monodentate ligands or T and Q together form a diketoenolate unit or a $C_2$- or $C_3$-alkylene unit having a methyl ketone end group or a linear $C_1$–$C_4$-alkylester or nitrile end group, A is a noncoordinating or weakly coordinating anion, x, p are 0, 1, 2 or 3 and q, n are 1, 2 or 3.

13. The compound of claim 12, wherein $R^2$ and $R^4$ are, independently of one another, 2,6-diphenyl-, 2,6-di(4'-methylphenyl)-, 2,6-di(4'-butyl-phenyl)-, 2,6-di(4'-methoxyphenyl)-, 2,6-bis-(3',5'-dimethyl-phenyl)- or 2,6-bis(2',4',6'-trimethylphenyl)phenyl, 2,5-diphenyl-, 2,5-di(4'-methylphenyl)-, 2,5-di(4'-t-butyl-phenyl)-, 2,5-di-(4'-methoxyphenyl)-, 2,5-bis-(3',5'-dimethyl-phenyl)- or 2,5-bis(2',4',6'-trimethylphenyl)pyrrolidyl, or 2,5-diphenyl-, 2,5-di(4'-methylphenyl)-, 2,5-di(4'-t-butyl-phenyl)-, 2,5-di(4'-methoxyphenyl)-, 2,5-bis(3',5'-dimethyl-phenyl)- or 2,5-bis(2',4',6'-trimethylphenyl)pyrrolide.

14. The compound of claim 12, wherein $R^2$ and $R^4$ are both 2,6-diphenylphenyl and m is 0.

15. The compound of claim 14, wherein $R^1$ and $R^3$ are hydrogen or methyl.

16. The compound of claim 12, wherein $R^2$ and $R^4$ are both [2,6-bis(4-t-butylphenyl)phenyl] and m is 0.

17. The compound of claim 16, wherein $R^1$ and $R^3$ are hydrogen or methyl.

18. A process for the polymerization of olefins which comprises contacting one or more polymerizable olefins with a compound of formula

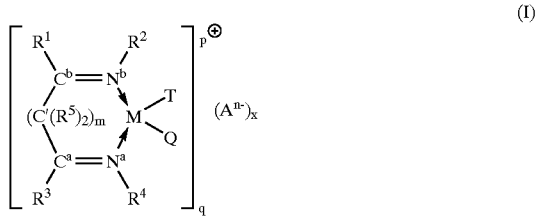

(I)

and optionally one or more cocatalysts, and $R^1$, $R^3$ are hydrogen, $C_1$–$C_{20}$-alkyl, $C_3$–$C_{10}$cycloalkyl, $C_6$–$C_{16}$-aryl, alkylaryl having from 1 to 10 carbon atoms in the alkyl part and from 6 to 16 carbon atoms in the aryl part, $Si(R^6)_3$, $N(R^6)(R^7)$, $OR^6$, $SR^6$, or $R^1$ and $R^3$ together with $C^a$, $C^b$ and, if present, $C'$ form a five-, six- or seven-membered aliphatic or aromatic, substituted or unsubstituted carbocyclic or heterocyclic ring, $R^2$, $R^4$ are $C_4$–$C_{16}$-heteroaryl or $C_6$–$C_{16}$-aryl bearing $C_4$–$C_{16}$-heteroaryl or $C_6$–$C_{16}$-aryl substituents in the two vicinal positions relative to the linkage point to $N^a$ or $N^b$, $R^5$ is hydrogen, $C_1$–$C_{10}$-alkyl, $C_6$–$C_{16}$-aryl or alkylaryl having from 1 to 10 carbon atoms in the alkyl part and from 6 to 16 carbon atoms in the aryl part, $R^6$, $R^7$ are $C_1$–$C_{10}$-alkyl, $C_6$–$C_{16}$-aryl or alkylaryl having from 1 to 10 carbon atoms in the alkyl part and from 6 to 16 carbon atoms in the aryl part, m is 0 or 1, M is a metal of group VIIIB of the Periodic Table of the Elements, T, Q are uncharged or monoanionic monodentate ligands or T and Q together form a diketoenolate unit or a $C_2$- or $C_3$-alkylene unit having a methyl ketone end group or a linear $C_1$–$C_4$-alkylester or nitrile end group, A is a noncoordinating or weakly coordinating anion, x, p are 0, 1, 2 or 3 and q, n are 1, 2 or 3.

19. The process of claim 18 which is carried out in the presence of hydrogen.

20. The process of claim 18 which is carried out at a temperature of −40° C. to 160° C.

21. The process of claim 20 which is carried out in the presence of hydrogen.

22. The process of claim 18 which is conducted in the presence of one or more cocatalysts.

23. The process of claim 22, wherein the cocatalyst is an aluminum alkyl, a haloaluminum alkyl, or an alumoxane.

24. The process of claim 23, wherein the alumoxane is methyl alumoxane.

25. The process of claim 18, wherein $R^2$ and $R^4$ are, independently of one another, 2,6-diphenyl-, 2,6-di(4'-methylphenyl)-, 2,6-di(4'-t-butyl-phenyl)-, 2,6-di(4'-methoxyphenyl)-, 2,6-bis-(3',5'-dimethyl-phenyl)- or 2,6-bis(2',4',6'-trimethylphenyl)phenyl, 2,5-diphenyl-, 2,5-di(4'-methylphenyl)-, 2,5-di(4'-t-butyl-phenyl)-, 2,5-di-(4'-methoxyphenyl)-, 2,5-bis-(3',5'-dimethyl-phenyl)- or 2,5-bis(2',4',6'-trimethylphenyl)pyrrolidyl, or 2,5-diphenyl-, 2,5-di(4'-methylphenyl)-, 2,5-di(4'-t-butyl-phenyl)-, 2,5-di(4'-methoxyphenyl)-, 2,5-bis(3',5'-dimethyl-phenyl)- or 2,5-bis(2',4',6'-trimethylphenyl)pyrrolide.

26. The process of claim 18, wherein $R^2$ and $R^4$ are both 2,6-diphenylphenyl and m is 0.

27. The process of claim 26, wherein $R^1$ and $R^3$ are hydrogen or methyl.

28. The process of claim 18, wherein $R^2$ and $R^4$ are both [2,6-bis(4-t-butylphenyl)phenyl] and m is 0.

29. The process of claim 28, wherein $R^1$ and $R^3$ are hydrogen or methyl.

30. The process of claim 18, wherein M is Pd or Ni.

31. The process of claim 30, wherein Q and T are chloride, bromide or iodide.

32. The process of claim 18, wherein M is Ni.

33. The process of claim 18, wherein one of the one or more polymerizable olefins is ethylene.

34. The process of claim 33, wherein ethylene is the only polymerizable olefin.

35. The process of claim 18, wherein a polymerizable olefin comprising a functional group is present.

36. The process of claim 18, which is carried out in a liquid phase.

37. The process of claim 18, which is carried out in a gas phase.

38. The process of claim 37, wherein the compound and optionally one or more of the cocatalysts are supported on a carrier.

39. The process of claim 18, wherein the compound and optionally one or more of the cocatalysts are supported on a carrier.

* * * * *